(12) United States Patent
Cronk

(10) Patent No.: US 8,231,863 B2
(45) Date of Patent: Jul. 31, 2012

(54) CONTINUOUS SPRAY SCALP THERAPY AND DISPENSING SYSTEMS FOR SAME

(76) Inventor: Peter J. Cronk, Moorestown, NJ (US)

(*) Notice: Subject to any disclaimer, the term of this patent is extended or adjusted under 35 U.S.C. 154(b) by 0 days.

(21) Appl. No.: 13/213,619

(22) Filed: Aug. 19, 2011

(65) Prior Publication Data

US 2011/0301554 A1 Dec. 8, 2011

Related U.S. Application Data

(60) Division of application No. 12/193,153, filed on Aug. 18, 2008, now Pat. No. 8,021,649, which is a continuation-in-part of application No. 11/677,777, filed on Feb. 22, 2007, now abandoned.

(51) Int. Cl.
*A61K 9/12* (2006.01)
(52) U.S. Cl. ........................................................ 424/45
(58) Field of Classification Search ........................ None
See application file for complete search history.

(56) References Cited

U.S. PATENT DOCUMENTS

| | | |
|---|---|---|
| 3,581,941 A | 6/1971 | Bruce |
| 3,731,854 A | 5/1973 | Casey |
| 4,828,837 A | 5/1989 | Uster et al. |
| 5,030,442 A | 7/1991 | Uster et al. |
| 5,035,351 A | 7/1991 | Moran |
| 5,040,704 A | 8/1991 | Moran |
| 5,106,609 A | 4/1992 | Bolich, Jr. et al. |
| 5,137,186 A | 8/1992 | Moran |
| 5,169,037 A | 12/1992 | Davies et al. |
| 5,211,316 A | 5/1993 | Adalberto et al. |
| 5,225,189 A | 7/1993 | Pena |
| 5,407,944 A | 4/1995 | Goldman |
| 5,489,047 A | 2/1996 | Winder |
| 5,490,630 A | 2/1996 | Hecker |
| 5,545,734 A | 8/1996 | Baker et al. |
| 5,587,148 A | 12/1996 | Mitchell et al. |
| 5,588,564 A | 12/1996 | Hutson et al. |
| 5,620,980 A | 4/1997 | Samour |

(Continued)

FOREIGN PATENT DOCUMENTS

WO  PCT/IL2007/000565   11/2007

OTHER PUBLICATIONS

Beauty Packaging Buyers' Guide, Beauty Packaging Magazine Online, Nov. 20, 2006, 2 pages.

(Continued)

*Primary Examiner* — Johann Richter
*Assistant Examiner* — Thor Nielsen
(74) *Attorney, Agent, or Firm* — Duane Morris LLP

(57) ABSTRACT

A spray delivery system in combination with a scalp medication is provided which includes a portable container having a gas imperious container wall, a pressure source disposed within the container, and a selectively operable valve assembly affixed to the container. The scalp medication is in liquid form and is disposed within the container. The scalp medication comprises a hair growth stimulation or hair growth maintenance active ingredient in an amount sufficient to stimulate or maintain hair growth disposed within a pharmacologically acceptable carrier solution. The valve assembly of the system produces a 1 mL spray of said scalp medication within about 5 seconds following a single operation of said valve assembly. A method of treating alopecia using a continuous spray employing such a system is also provided. Both bag-on-valve (bag-in-can) and metered dose packages are disclosed.

4 Claims, 2 Drawing Sheets

U.S. PATENT DOCUMENTS

| | | | |
|---|---|---|---|
| RE35,540 | E | 6/1997 | Davies et al. |
| 5,653,965 | A | 8/1997 | Narayanan et al. |
| 5,889,054 | A | 3/1999 | Yu et al. |
| 5,989,529 | A | 11/1999 | Kaplan |
| 5,994,319 | A | 11/1999 | Hoke, Jr. |
| 6,039,306 | A | 3/2000 | Pericard et al. |
| 6,129,080 | A | 10/2000 | Pitcher et al. |
| 6,165,450 | A | 12/2000 | Chaudhuri et al. |
| 6,168,781 | B1 | 1/2001 | Ukaji et al. |
| 6,255,313 | B1 | 7/2001 | Suzuki et al. |
| 6,395,269 | B1 | 5/2002 | Fuller et al. |
| 6,420,352 | B1 | 7/2002 | Knowles |
| 6,436,377 | B1 | 8/2002 | Hansenne et al. |
| 6,465,514 | B1 | 10/2002 | Hallam et al. |
| 6,627,216 | B2 | 9/2003 | Brandt et al. |
| 6,723,744 | B2 | 4/2004 | Aspnes et al. |
| 6,783,027 | B2 | 8/2004 | Hilvert et al. |
| 6,926,208 | B2 | 8/2005 | Ivri |
| 2002/0139383 | A1 | 10/2002 | Christensen |
| 2004/0204433 | A1 | 10/2004 | Imamura et al. |
| 2005/0037060 | A1 | 2/2005 | Wai-Chiu So |
| 2005/0043283 | A1 | 2/2005 | Fares |
| 2005/0098588 | A1 | 5/2005 | Dunne |
| 2007/0059265 | A1 | 3/2007 | Boulle |
| 2007/0141004 | A1 | 6/2007 | Malek |
| 2007/0290007 | A1 | 12/2007 | Eberhardt |
| 2008/0038206 | A1 | 2/2008 | Steinbrecht et al. |
| 2009/0032617 | A1 | 2/2009 | Withers |

OTHER PUBLICATIONS

ABS® Bag-in-Can System, CCL Container, www.cclcontainer.com, Nov. 20, 2006, 2 pages.
Eastern Aerosol Association Upcoming Events, Fall Meeting—Alternative Packaging Showcase, www.easternaerosol.com, Nov. 20, 2006, 4 pages.
Latest Aluminum Containers Test Markets, Aluminum Now Online, vol. 8, No. 4, Jul./Aug. 2006, 4 pages.
Rogaine Foam, Abby's Hair Loss Products, AbbysGuide.com, 1998-2006, 1 page.
"Makers of Rogaine® Revolutionize the Hair Loss Treatment Industry Once Again: New, innovative foam application is fast, easy and convenient," Pfizer Consumer Healthcare, www.pfizerch.com, 2005-2006, 2 pages.
Aerosol Continuous Spray Sunscreen, Very Water Resistant SPF 30+ (Tested) 13505-52, National Starch, Personal Care, www.personalcarepolymers.com, Oct. 23, 2006, 1 page.
Coppertone Kids Continuous Spray Sunscreen Spf 50, PriceGrabber. com, Nov. 20, 2006, 1 page.
Dermacryl® 79 (28-4979), National Starch & Chemical, Personal Care Product Overview, www.personalcarepolymers.com, Nov. 20, 2006, 1 page.
Product Review: Rogaine Foam, Hair Loss Q & A Blog, www.regrowhair.com, Nov. 20, 2006, 5 pages.
New Technology in Sun Protection, Dental and Health Articles, DentalPlans.com, Oct. 24, 2006, 4 pages.
Goodbye to the Beach Battle: Coppertone Kids® Continuous Spray SPF 50 Makes Sunscreen Application Easier for Parents, Schering-Plough News Release, www.schering-plough.com, 2003-2006, 2 pages.
Bernstein Medical—Rogaine (Minoxidil), Medical Hair Loss Treatments, Bernstein Medical, Center for Hair Restoration®, www.bernsteinmedical.com, Jan. 3, 2007, 3 pages.
Chia-Ming Chiang et al., "Bioavailability assessment of topical delivery systems: Effect of vehicle evaporation upon in vitro delivery of minoxidil from solution formulations," International Journal of Pharmaceutics 55(2-3): 229-236, Deep Blue at the University of Michigan, www.deepblue.lib.umich.edu, Oct. 15, 1989, 2 pages.
More "Firsts" from CCL Container Earns Worldstar Acclaim, CCL Container Media Resource Center, www.cclcontainermedia.com, Nov. 20, 2006, 3 pages.
Connetics Licenses Foam Delivery Technology to Pharmacia for Use With Rogaine®, Connetics Corporation: Investor Relations, www.connetics.com, 2002, 2 pages.
Men's Rogaine® Foam, Product Description, Pfizer Consumer Healthcare, www.pfizerch.com, Nov. 20, 2006, 5 pages.
"Aerosol" definitions, encyclopedia descriptions and translations, Answers.com, Nov. 20, 2006, 6 pages.
Goodbye to the Beach Battle: Coppertone Kids® Continuous Spray SPF 50 Makes Sunscreen Application Easier for Parents, SpecialChem, Innovation & Solution in Cosmetics, Sun Care News, May 10, 2006, 2 pages.
CCL Container Honored by New Jersey Packaging Executives, CCL Container Media Resource Center, www.cclcontainermedia.com, 2006, 3 pages.
Proven Treatments for Men's Hair Loss, www.hairlosstalk.com, 1999-0002, 4 pages.
S. Tata, N. Weiner and G. Flynn, "Relative Influence of Ethanol and Propylene Glycol Cosolvents on Deposition of Minoxidil Into the Skin," J. Pharm Sci, Oct. 1994;83(10):1508-10, NCBI, PubMed, www.pubmed.gov, abstract, 1 page.
S. Tata, G.L. Flynn and N.D. Weiner, "Penetration of Minoxidil from Ethanol/Propylene Glycol Solutions: Effect of Application Volume and Occlusion," J. Pharm Sci, Jun. 1995;84(6):688-91, NCBI, PubMed, www.pubmed.gov, abstract, 1 page.
Topical Minoxidil, Topicals—Active Forum, www.farrellmanual.com, Jan. 3, 2007, 4 pages.
Other Helpful Treatments for Men's Hair Loss, Product Summaries, www.hairlosstalk.com, Jan. 3, 2007, 4 pages.
Hair Loss: DMI or Dimethyl Isosorbide (solvent or penetrant), www.hairsite.com, Jan. 3, 2007, 2 pages.
Minoxidil, Entry from Wikipedia, The Free Encyclopedia, Jan. 3, 2007, 3 pages.
S.E. Whitmore, "The importance of proper vehicle selection in the detection of minoxidil sensitivity," Archives of Dermatology, vol. 128, No. 5, May 1992, abstract, 1 page.
Minoxidil, entry from HealthAtoZ, www.healthatoz.com, Jan. 3, 2007, 5 pages.
Minoxidil—Rogaine for Men vs. Rogain for Women, Bernstein Medical Hair Transplant Blog—Bernstein Medical, Center for Hair Restoration®, www.bernsteinmedical.com, Aug. 11, 2006, 3 pages.
Topical Minoxidil, product descriptions, www.farrellmanual.com, Jan. 3, 2007, 4 pages.
Product Review—Minoxidil (Rogaine) for Women, Consumer Hair Loss Information, www.hairlosstalk.com, Jan. 3, 2007, 3 pages.
New Rogaine Foam Product Soon to be a Reality, HairLossHelp, Hair Loss News, www.hairloss.help.com, Nov. 20, 2006, 4 pages.
Letter from James E. Davenport of Patent & Trademark Searches, Inc. to Peter Cronk dated Mar. 19, 2007, regarding patent search results.
International Search Report and Written Opinion dated May 22, 2008 in PCT/US08/54754.
International Search Report and Written Opinion dated Nov. 17, 2008 in PCT/US08/73550.
International Preliminary Report on Patentability and Written Opinion dated Feb. 22, 2011 in PCT/US08/73550.
Office Action dated Oct. 28, 2010 in U.S. Appl. No. 11/677,777.
Klein, Oscar, "Hair Loss Treatment Study", Clinical Study, 2008, pp. 1-5, www.hairgrowthmd.com/clinical_study.php.
Klein, Oscar, Product Directions, 2008, pp. 1-4, www.hairgrowthmd.com/directions.php.

CONTINUOUS SPRAY SCALP THERAPY AND DISPENSING SYSTEMS FOR SAME

CROSS-REFERENCE TO RELATED APPLICATIONS

The present invention is a divisional of U.S. application Ser. No. 12/193,153, filed Aug. 18, 2008 now U.S. Pat. No. 8,021,649, which is a continuation-in-part of U.S. application Ser. No. 11/677,777, filed Feb. 22, 2007 now abandoned, the entirety of which is incorporated herein by reference.

FIELD OF THE INVENTION

The present invention relates to scalp medications generally, and particularly those for treating alopecia.

BACKGROUND OF THE INVENTION

Alopecia, the loss of hair in men and women, involves a gradual decrease of scalp hair density in adults, with a transformation of terminal to vellus hairs which become lost as a result of familial increased susceptibility of hair follicles to androgen secretion following puberty. Two areas of the scalp are commonly affected in men, as evidenced by a receding frontal and bilateral triangular temple hair lines, and a balding patch on the vertex, which may progress to complete male pattern baldness. In females, a diffuse partial hair loss in the central parietal area of the scalp with preservation of the frontal and temporal hair lines is most common.

One of the more common therapies for alopecia is minoxidil, which has been proven to be an effective hair growth stimulator that can both maintain and increase scalp hair counts. Minoxidil was first used as a patent antihypertensive drug. It was later discovered that Minoxidil had positive effects on hair growth when applied topically to the scalp. Minoxidil was first mass marketed as Rogaine® lotion by Upjohn, Inc. for the treatment of hair loss in the late 1980s. Rogaine® lotion still remains the only FDA approved topical medication for the treatment of hair loss in the United States, as of this date. The directions associated with traditional minoxidil lotions, such as Rogaine®lotion, now manufactured by Johnson and Johnson, is that a total dose of 1 mL minoxidil topical solution should be applied twice per day to the scalp, beginning at the centre of the affected area. Each 1 mL of minoxidil solution contains 20 mg of minoxidil for 2% solutions and 50 mg of minoxidil for 5% solutions. This dose should be used regardless of the size of the affected area. The total daily dose should not exceed 2 mL. The method of application varies according to the disposable applicator used. Packages contain several applicator options, including a dropper marked with a 1-mL calibration, a spray applicator, and an extended-spray applicator, which is ideal for long hair. Six pumps of the applicators release 1 mL of minoxidil. Because systemic absorption could affect blood pressure, the patient should not inhale the aerosol generated by the spray applicators.

Although the following systemic effects have not been associated with the topical use of minoxidil topical solution, there is some absorption of minoxidil from the skin and the potential exists for systemic effects such as tachycardia, angina, edema or potentiation of the orthostatic hypotension produced by guanethidine. Systemically absorbed minoxidil is secreted in human milk.

The application times for minoxidil should be at least four hours apart, suggesting that the best times to apply the product would be right after the morning shower, and before bed at night. The traditional 5% minoxidil Rogaine® lotion utilizes as much as 50% by volume propylene glycol (20% v/v of propylene glycol for 2% minoxidil) as a vehicle for extending the delivery of the active medication to the scalp, and for ensuring that the applied minoxidil is evenly spread across the affected area and easily absorbed into the skin. Propylene glycol and ethanol alcohol are also used to solubilize minoxidil. The problem associated with smearing copious amounts of propylene glycol on one's scalp is that it leaves the hair and scalp with a greasy texture for an extended period of time after the application. The resulting appearance is often unflattering. It also leaves the hair looking matted down and even thinner than it really is, which may be considered an unfortunate step in the wrong direction for a hair loss treatment.

Another issue associated with propylene glycol is that it can irritate the user's scalp, resulting in itching, flaking, redness of the scalp, oiliness of the scalp, excessive dandruff, and even peeling in some cases. Because of these effects, the use of traditional minoxidil solution was not an option for many hair loss sufferers, and glycerine versions of the popular medication have been developed, available by prescription from Minoxidil.com.

Johnson and Johnson is currently marketing Rogaine® Foam, which delivers minoxidil to the scalp in a manner that is just as effective as the traditional propylene glycol based minoxidil lotions, but without some of the mess or unpleasantness. Rogaine® Foam is designed to retain its "foamy" texture at room temperature, but quickly liquefies, spurring quick skin absorption at body temperature.

Fast skin absorption by Rogaine® Foam means that the active ingredient of Rogaine® Foam, minoxidil, will be readily absorbed into the hand of the user, where it clearly is not intended to be absorbed. Over-absorption of minoxidil can result in vision changes, chest pain and fast or irregular heart beat. Women exposed to over-absorption of minoxidil may experience additional unwanted facial hair growth. Additionally, minoxidil may pass from mother to child through breast milk. It is for these and other reasons that the Rogaine® Foam package insert suggests that the user rinse his or her hand under cold water before applying the foam, to slow down absorption of the active ingredient into the hand. This, of course, requires another step (or two, if the user also dries his or her hand, as recommended by the manufacturer) in the application of the medication. It may also dilute the concentration if one does not immediately dry one's hand after wetting, and before applying the foam. In addition, hair does feel a little stiffer after the application of the Rogaine® Foam and the smearing of the foamy application, with or without a wet hand, can also mat down hair styles, making them less natural looking.

Accordingly, there remains a need for further dispensing systems and methods for scalp medications, including minoxidil and other products, such as DHT inhibitors, finesteride (Propecia®), copper peptides (Tricomin® and Folligen®), other DHT inhibitors (Dutasteride®), all-around treatments or combinations (Proxiphen®) androgen receptor blockers (Spirondactone®), corticosteroids, vitamin A derivatives (Retin-A®), tretinoin, azelaic acid, zinc, B6, grape seed extract, nicotinate and/or progesterone, which are easy to use and provide a more natural appearance than conventionally applied propylene glycol-based and foam-based products delivery systems.

SUMMARY OF THE INVENTION

In a first embodiment of the present invention, a spray delivery system in combination with a scalp medication is provided. The system includes a portable container having a gas impervious container wall, a pressure source disposed within the container and a selectively operable valve assembly affixed to the container. The scalp medication is in liquid form and is disposed within the container. It further comprises a hair growth stimulator or hair growth maintenance active ingredient in an amount sufficient to stimulate or maintain hair growth disposed within a pharmacologically acceptable carrier solution. The valve assembly produces a 1 mL spray of said scalp medication within about 5 seconds following a single operation of said valve assembly.

In a more preferred embodiment of the present invention, the scalp medication comprises about 2-15% minoxidil or about 20 mg to about 150 mg minoxidil per mL (2%-15% minoxidil). If a continuous spray package is employed the spray is non-chilling (98.6° F.±5° F.), upon contact with skin, and is delivered quietly, under 60 decibels. The valve assembly can be a 2-way valve, to enable both delivery of the scalp medication and charging of the medication into the container, or product bag. More preferably the valve assembly produces a 1 mL spray of scalp medication within about 1-5 seconds during a single operation of the valve assembly, for an effective delivery rate of about 0.2-1 mL/second. This would be a significant improvement over currently available spray applicators used for generic minoxidil, which are known to require up to six pumps of a pump dispenser to release 1 mL of minoxidil solution.

In a further embodiment of the present invention, a method of treating alopecia is provided. The method includes providing a delivery system comprising a valve assembly affixed to a portable container containing a pressure source surrounding a product bag containing minoxidil in an amount sufficient to stimulate or maintain hair growth, said minoxidil disposed within a pharmacologically acceptable carrier solution. The method further includes rotating the container and the valve assembly such that the valve assembly is at least partially below a portion of the container, actuating the valve assembly whereby the pressure source surrounding the product bag is used to force minoxidil and the carrier solution out of the bag and continuously spraying a fine mist of said minoxidil and said carrier solution onto an alopecia affected area of the scalp, whereby said fine mist contains about 1 mL of said minoxidil and said carrier solution and said continuous spraying step is less than about 5 seconds in duration for an effective delivery rate of greater than 2 mL/second. This method can be further employed in a continuous spraying step which is about 1-5 seconds, preferably about 1-3 seconds, and more preferably, about 2 seconds in duration during a single operation of the valve assembly. Preferably, the delivery system delivers a mist or spray which results in less than 5% of the droplets in the mist or spray being respirable when the mist or spray is directed at a scalp.

In further improvements, the valve assembly can be selected to have an actuator valve diameter of less than 0.10 inches, preferably greater than about 0.001 inches, and more preferably, about 0.001 inches to about 0.015 inches. This range enables the spray to be delivered efficiently within the time constraints of typical use by consumers of spray products of about 2 seconds. It is also desirable to maintain the actuator diameter within these preferred ranges so that the spray droplets and volume are not so large as to cause dripping and runniness of the product, but just large enough to avoid the creation of too many respirable droplets.

In a further embodiment of the present invention, a continuous fine mist spray medication delivery system is provided. This system includes a selectively operable valve assembly affixed to a portable container containing a pressurized agent or pressure source and a product bag containing said spray medication. The product bag, also located in the container, includes a sheet of gas impervious material having a barrier layer therein. The gaseous propellant is substantially separated from the medication and its liquid carrier, at least prior to, and more preferably, prior to and after selective operation of the valve assembly to produce the fine mist. The continuous spray fine mist medication preferably comprises a hair growth stimulator or maintenance active ingredient, such as minoxidil, a DHT inhibitor, an androgen blocker, or other combinations thereof, in an amount sufficient to stimulate or maintain hair growth, or both, disposed within a pharmacologically acceptable solution, for example, alcohol, with or without propylene glycol, glycerin, dimethyl-isosorbide, or other "extenders" to permit better absorption.

It has been suggested that minoxidil is dose dependent, meaning that patients may have to increase the concentration of minoxidil over time in order to sustain the results. Consequently, it has been suggested that people should start using a lower strength formula, such as 2% v/v, and gradually move up the scale to 5% v/v, and then ultimately, to 12% v/v.

The present invention employs advanced spray technology to provide a quick, easy and effective application of scalp medications. In a preferred embodiment, a continuous spray of fine mist medication can be provided at every angle, even upside down, enabling application to hard to reach places like the vertex of the scalp. The preferred spray technology uses environmentally safe, bag-in-can or metered dose technology to apply scalp medications, such as 2-15% v/v minoxidil (2,4-Diamino-6-piperidinopyrimidine 3-oxide) or DHT inhibitors, such as 5-alpha-reductase inhibitors, such as finesteride (such as Propecia® brand, available from Merck, which is not recommended for women who are or may potentially become pregnant), or dutasteride (such as Avodart®, available from GlaxoSmithKline), copper peptides (Tricomin® and Folligen® brands), all-around treatments or combinations (Proxiphen® brand), androgen receptor blockers (Spirondactone® brand), corticosteroids, Retin-A® brand, tretinoin, azelaic acid, zinc, B6, grape seed extract, nicotinate and/or progesterone. The delivery systems of this invention eliminate the uncomfortable twisting, reaching, and most of the hand-drug contact associated with applying conventional Rogaine® liquid or Rogaine® Foam to the back of one's scalp. Accordingly, the active scalp medications are easier to apply than Rogaine® lotion, even when compared to Rogaine® lotion dispensed from the pump-spray bottle, since the delivery system of this invention can preferably operate upside down without clogging or interruptions, and dispenses a preferred fine, even and continuous mist. Because this delivery system allows the scalp treatment to be applied evenly and continuously directly from the container onto the scalp, with little or no need for rubbing, absorption into the hand of the user, hand washing before and/or after use of the product, and unflattering matting of the hair due to rubbing can be eliminated.

The packaging of the bag-on-valve embodiments of this invention, preferably, also maintains total product integrity and freshness, and extends the useful life of the medication, even lengthening shelf-life. In addition, by using a preferred bag-in-can system, the scalp medication can be separated from the pressurizing agent within a preferred hermetically sealed, multi-layered laminated pouch. The pouch can maintain total formulation integrity, and pure product, preferably, can be dispensed without contamination by propellants. The spray medication can have a quiet and non-chilling discharge, and allows all attitude)(360° dispensing. By using existing through-the-valve aerosol filling technology and equipment, the dispensing system of this invention can be designed to work with standard actuators and aluminum aerosol cans.

In a further embodiment of the present invention, a medication is provided which includes a continuous even mist, including liquid droplets, having an average diameter of about 1 nanometer to about 2000 micrometers, said mist containing minoxidil in an amount sufficient to stimulate or maintain hair growth, in which said minoxidil is disposed within a pharmacologically acceptable carrier solution.

In a preferred embodiment of this invention, the spray medication can be delivered quietly, under 50-60 decibels, and the continuous spray is, preferably, non-chilling upon contact with skin, or is approximately at ambient temperature. The valve assembly can include a two-way valve and the container may comprise an aluminum or steel can. The bag, desirably, includes at least one gusset so that it can expand when product is introduced and lay on the bottom of the container to relieve stress on the valve assembly.

The above and other features of the present invention will be better understood from the following detailed description of the preferred embodiments of the invention that is provided in connection with the accompanying drawing.

BRIEF DESCRIPTION OF THE DRAWING

The accompanying drawing illustrates a preferred embodiment of the invention, as well as other information pertinent to the disclosure, in which.

DETAILED DESCRIPTION

Figure 1:
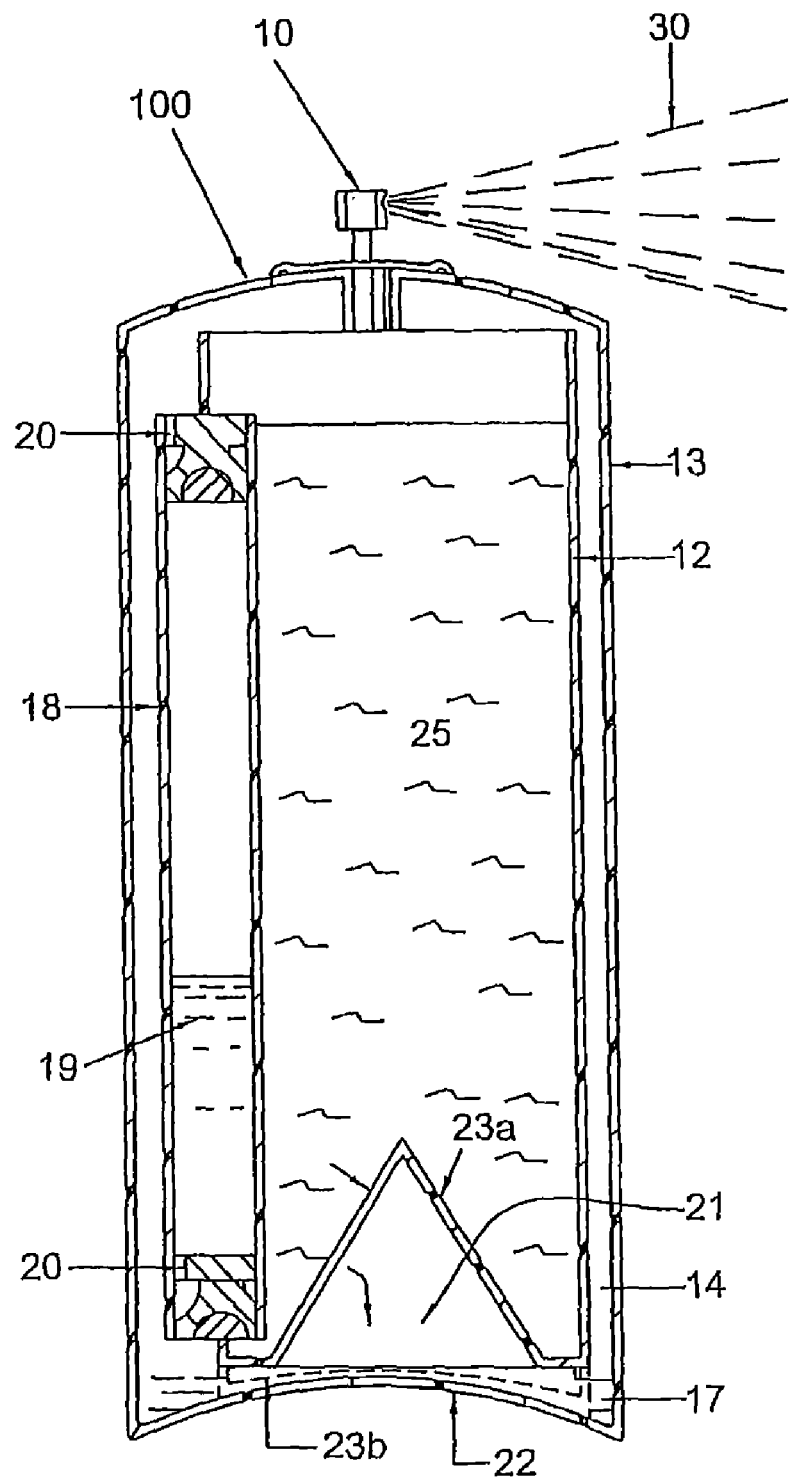
FIG. 1 is a cross-sectional side elevational view showing a dispensing system (with a continuous spray in phantom) for housing the liquid medication of this invention.

The present invention pertains to continuous spray medications, spray medication dispensing systems, and methods for treating alopecia, in which a continuous mist of a scalp medication, such as minoxidil, DHT inhibitors and/or androgen blockers, for example, is provided in an amount sufficient to stimulate or maintain hair growth, or both, for example. The minoxidil and/or other medication is disposed within a pharmacologically acceptable carrier solution.

In the preferred embodiments of this invention, the continuous mists are designed to generate liquid droplets that are readily absorbed through the dermis, especially scalp tissue. Mist particle sizes range from molecular clusters on the order of about 1 nanometer to about 2000 micrometers, and more preferably, the spray should provide good coverage of the surface area without running onto unwanted areas of the face and neck The preferred delivery system of the present invention includes the ABS bag-in-can system, such as the system available from CCL Container. These preferred systems are hand held, portable, and completely self-contained. The ABS bag-in-can system separates the product from the pressurizing agent with a hermetically sealed, multi-layered laminated pouch "bag". The bag maintains total formulation integrity, and only pure product, preferably, is dispensed, as opposed to other aerosol systems that can mix the product with the gaseous propellant. This maintains the total product integrity, such as alcohol mixtures, solutions and suspensions of minoxidil and fenesteride formulations, and potentially extends their shelf life. This system also has a quiet, non-chilling discharge, and allows for all-attitude)(360° dispensing, permitting "upside-down" dispensing, which is highly desirable for spraying one's scalp. While Rogaine® lotion comes with its own pump spray dispenser, the dispenser can not work upside down and, consequently, is very awkward to use on the vertex of one's scalp. Pump-spray containers such as this one are widely available and operate on the principle that when the nozzle pump is manually depressed, pressure is exerted on the liquid in the container, forcing it out of the spray nozzle. This pump dispenser is not continuous and produces a very uneven distribution of the product on one's scalp, generally depositing a shot of 0.5 mL or more of the ingredients, in a heavy squirt to a small area of the scalp, which tends to cause the liquid medication to run to where it is not needed, or worse, where it is definitely not recommended, such as on the face or the wearer's eyes. Moreover, conventional pump-spray dispensers such as these, attached to plastic bottles with plastic threads, are not hermetic, so the contents can be affected by environmental conditions, which, in some cases, reduce the efficacy of the medication, and/or its solvent (also referred to as the "extender" or "carrier" solution).

Alternatively, this invention can employ a piston barrier package (also available from CCL Container since 1991), which also assures separation of the scalp medication from the propellant or pressurizing agent, for maintaining the purity and integrity of the formulation throughout its consumer life span. The system provides smooth controlled and uniform discharge. In a piston barrier package, a piston is disposed in a preferred seamless tubular package between the propellant and the product. As the nozzle is activated, the piston is activated by the propellant pressure in the lower part of the container, to push out the product through the nozzle. The preferred CCL version of this system eliminates propellant bypass tendency common with other metal containers because of its seamless construction. It also comes with a specially engineered gassing hole at the bottom for improving sealing during gassing and plugging operations.

Still in a further alternative example of this invention, a metered-dose valve assembly can be used for dispensing the scalp medications of this invention. A metering valve typically regulates the volume of a formulation passing from a container to a metering chamber, which defines the maximum amount of the formulation that would be dispensed as the next dose. The metering chamber typically fills with the formulation prior to the patient actuating the valve stem and thereby releasing the dose. The metering chamber is refilled with formulation after dispensing one dose so that the metering valve is ready to discharge the next dose. The metering chamber contains a formulation at all times except for the brief time during which the valve stem is depressed by the user to discharge a dose. One example of a metered valve is disclosed in U.S. Pat. No. 6,783,027, which is hereby incorporated by reference.

In applying the proper amount of scalp medication to a consumer's scalp, the amount of hair growth stimulator or hair growth maintainer active that will ultimately be deposited must be considered. It is commonly desired to deliver from about 20 mg per mL (for 2% minoxidil solution) to about 50 mg per mL (for 5% minoxidil solution) to the scalp, regardless of the product form. In considering the use of spray packages (e.g., pressurized aerosol packages), it has been reported, see U.S. Pat. No. 6,783,027, that a typical consumer sprays consumer products such as antiperspirants (i.e., actuates the spray package) on average for 2 seconds, regardless of the amount of product being delivered because the consumer usually doesn't see the amount of product that is ultimately delivered. Therefore, when designing a package to spray a scalp medication, one must first adhere to this overriding consumer behavior of continuously spraying for 2 seconds. It is understood that spraying too much of a liquid or emission product may result in a wet runny cosmetic feel, while spraying too little of a liquid or emulsion product may result in a unacceptable efficacy results.

In certain formulations of the present invention, a clear, preferably no-rub, continuous spray of medication is provided. For example, an alcohol base with little or no propylene glycol can be used. Higher amounts of propylene glycol, such as the 50% by volume used in Rogaine® lotion, can leave one's hair feeling flat and greasy. Glycerin and dimethyl-isosorbide, or combinations of glycerin, dimethyl-isosorbide, and/or propylene glycol (such as 50%/50% v/v or w/w glycerin-propylene glycol, 80%/20% v/v or w/w glycerin-propylene glycol, 80%/10%/10% v/v/v or w/w/w dimethyl-isosorbide, glycerin and propylene glycol, or the like) are more preferred for use as solvents and extenders for this invention. It has been reported that when dipropylene glycol additions to minoxidil solutions are less than 5% by weight, the retention effect of minoxidil in the dermis is insufficient, and when the amount is more than 40% by weight, the resulting preparation gives a bad feeling in use. See U.S. Pat. No. 6,255,313.

In the preferred embodiments of this invention, the minoxidil formulations can include other ingredients, such as butane, butylated-hydroxytoluene, cetyl alcohol, citric acid, fragrance, glycerin, isobutane, lactic acid, polysorbate 60, propane, purified water, SD alcohol 40B, and stearyl alcohol. In other formulations, sunscreen additives can be added, such as butyl methoxydibenzoylmethane, homosalate, ethylhexylsalicylate, benzophenone-3, and diethylhexyl 2,6 naphthalate. If water resistance is required, acrylates/octylacrylamide copolymers (such as Dermacryl 79, available from National Starch) can be added.

In a further compositional embodiment, a minoxidil spray lotion formulation includes at least about 2% v/v or 0.1% w/w, and preferably, about 2-15% v/v or 0.1-10% w/w minoxidil in a carrier solution comprising butane, butylated hydroxytoluene, cetylalcohol, citrix acid, fragrance, glycerin, isobutane, lactic acid, polysorbate 60, propane, purified water, SD alcohol 40B and stearyl alcohol.

In still a further embodiment, a minoxidil spray lotion formulation includes about 2% v/v or 0.1% w/w, preferably about 2-15% v/v or 0.1-10% w/w minoxidil in a carrier solution comprising about 60% v/v or w/w alcohol, about 20-50% v/v or w/w propylene glycol or glycerin and purified water (balance). For greater sustained release, dipropylene glycol can be used, as shown in U.S. Pat. No. 6,255,313, which is hereby incorporated by reference. Gel formulations containing minoxidil are also contemplated by this invention and disclosed in U.S. Pat. No. 5,225,189, which is also hereby incorporated by reference.

The preparations of the present invention are preferably adjusted to a pH of 4-9, and more preferably about 5-8 when diluted with purified water.

In more preferred embodiments of this invention, a continuous fine mist spray medication dispensing system 100 is provided, as shown in FIG. 1. The dispensing system includes a selectively operable valve assembly 10 affixed to a container containing a pressure source or pressurizing agent. A product bag 12 containing said medication 25 in a liquid form is also provided. The bag 12 is disposed within the container and includes a sheet of gas impervious material having a barrier layer therein. The gas impervious material helps to separate the medication 25 in liquid form from the pressure source or pressurizing agent located elsewhere in the container, so as to keep the medication fresh and efficacious.

The fine spray mist medication is preferably, delivered quietly, under 60 decibels (normal conversation, sewing machine, typewriter), and more preferably, less than 40 decibels, or most preferably, about 30 decibels or less (whisper, quiet library). It is a fine spray which is, preferably, non-chilling upon contact with skin, e.g., 98.6° F.±5° F. The valve assembly 10 is, preferably, a two-way valve. The container is preferably made of a metal, such as aluminum or steel. The bag 12 preferably includes at least one gusset 21 which expands from a position of 23a to a position 23b when the liquid medication 25 reaches a full level, at which time a fine mist 30 can be sprayed.

In a further embodiment of the present invention, a method of treating alopecia is provided comprising a delivery system which includes a valve assembly 10 affixed to a container 13 containing a pressure source or pressurized agent, and a product bag containing minoxidil in an amount sufficient to stimulate or maintain hair growth disposed within a pharmacologically acceptable carrier solution. The container 13 is then rotated, and the valve assembly 10 is located such that the valve assembly 10 is at least partially below a portion of the container 13, or even upside down. The method further includes continuously spraying a fine mist of said minoxidil and said carrier solution onto an alopecia affected area of the scalp. The applied solution is evenly distributed and no further action or rubbing is required, but some minor rubbing can be employed, if necessary, to reach spots missed by the initial application.

In the preferred embodiments of the present invention, the pharmacologically acceptable carrier solution contains less than about 50% v/v propylene glycol, and more preferably, less than about 20% v/v, and most preferably, less than about 5% v/v propylene glycol, or none at all. The carrier solution can also include, or alternatively comprise, glycerin, dimethyl-isosorbide, or a combination thereof, purified water and an alcohol, such as SD alcohol, ethanol or isopropanol.

In still a further embodiment of the present invention, a spray medication is provided which includes an even, continuous mist containing a scalp medication sufficient to stimulate or maintain hair growth. This embodiment of the scalp medication is disposed within a pharmacologically carrier solution. This spray medication is transparent on the scalp and does not need to be rubbed into the skin of the scalp to be effective in stimulating or maintaining hair growth. This medication embodiment also, preferably, contains less than 20% v/v propylene glycol for a 2% minoxidil solution.

With further reference to FIG. 1, the product dispensing system 100 incorporates a product dispensing bag 12 in accordance with the preferred embodiment of the present invention. The system includes a container 13 having external wall surface. A product dispensing bag 12 has a gusseted bottom 23 and sealed side portion or portions. The product dispensing bag 12 is also sealed around its top edge. A valve assembly 10 is attached to the product dispensing bag 12 via a valve connector extending into the top surface of the container 13. FIG. 1 illustrates a side elevational view of the product dispensing bag 12 showing the bag being partially filled. The gusset 23a can be opened, and then the expanded gusset 23b can rest on the dome-shaped bottom 22.

After the container 13 is sealed, product is injected into the product dispensing bag via the preferred two-way valve and valve connector. As the bag 12 fills, it expands, and the gusseted bottom 23 spreads along the surface 22 of the bottom of the container 13. The gusseted bottom 23 serves to prevent undue force on the seal between the valve 10 and the bag 12 when product is in the bag 12, because the mass of the product preferably rests on the bottom of the container, rather than being supported by the bag/valve interface if the bag hangs in free space. The gusseted bottom 23 controls the fill operation so that the bag fills more evenly and more fully. Furthermore, the gusset 23 improves bag fill capacity for a given container size. Preferably, the height of the gusset 23a (the distance between the bottom of the bag and the interior seam of the gusset) extends for approximately eighty percent (80%) of the radius of the container 13.

It is further necessary to provide a source of dispensing pressure in the container. In one method and system for providing a dispensing pressure that is regulated, a gas chamber consisting of the region in the closed container surrounding the product bag 12, can be charged to an initial dispensing pressure. The pre-charge exerts pressure on the product dispensing bag 12 so that when the valve 10 is activated, product is forced from the bag 12 and out of the container 13. Without regulation, the pressure may steadily decline as product is dispensed. Such a pre-charge can be provided by using compressed gas in the container surrounding the product bag, or by using a liquefied gas propellant.

The preferred product dispensing bag and dispensing system of the present invention is further described in U.S. Patents Re. 35,540; 5,169,037 and 5,035,351, which are all hereby incorporated herein.

FIG. 1 further illustrates one type of a dispensing system configuration wherein the product dispensing bag 12 of the present invention is used with a pressure regulating mechanism. As described above, the product dispensing bag of the present invention can also be used in such systems as compressed gas or liquefied hydrocarbon systems or any product-in-bag dispensing system where a pressure source surrounding the bag is used to force product out of the bag, so that a continuous spray 30 can be generated.

A product bag 12 having a gusseted bottom is disposed within container walls 13. A gas generating chamber 14 is preferably defined by the area bounded by the container walls 13 and the exterior of the product bag 12. A first reactant 17, such as sodium bicarbonate, is disposed in a bottom of the container in the gas generating chamber 14 and a pressure regulating, mechanism 18 is also disposed in the gas generating chamber. The pressure regulating mechanism 18 includes a second reactant 19 which can be a liquid reactant, such as citric acid or vinegar. In one embodiment, the pressure regulating mechanism is a hollow tube having check valves 20 disposed at either end. When the second reactant 19 combines with the first reactant, gas is generated within the gas generating chamber 14. The pressure regulating mechanism 18 is designed so that when a pressure outside of the tube exceeds a pressure inside of the tube, gas enters into the tube until pressure equilibrium is established. When the pressure inside of the tube exceeds the pressure outside of the tube, the second liquid reactant 19 is forced from the tube into the gas generating chamber 14 so as to react with the first reactant 17 to thereby generate gas within the gas generating chamber and reestablish pressure equilibrium between the pressure inside of the tube and the pressure surrounding the tube. The pressure generated in the gas generating chamber 14 places the product bag 12 under pressure and, hence, also places the product 25 disposed within the bag 12 under pressure as well. Thus, when valve 10 is activated so as to dispense product 25, product 25 is dispensed from the container under pressure produced in the gas generating chamber.

While, preferably, sodium bicarbonate is used as the first reactant, and citric acid as the second reactant, other reactants may be used. Also, solutions and slurries of the reactants may be used and the reactants may be interchanged, if desired.

The pressure regulating mechanism system 18 will be described in greater detail below. However, the tube is designed in such a manner so as to react with the first reactant 17 to maintain a substantially constant dispensing pressure throughout the dispensing of the entire product disposed in the product bag 12.

The initial pressure of the dispensing system is set when the product bag 12 is filled. As product 25 is introduced into the bag 12, the volume of the bag 12 expands, thereby reducing the volume of the gas generating chamber to, in turn, increase the pressure within that chamber. The increase in pressure of the chamber, in turn, results in an increase in the gas pressure within the pressure regulating mechanism 18. When the product bag 12 has been filled with product, a specific pressure is set in the gas generating chamber 14, and a gas pressure is also set in the pressure regulating mechanism 18 as equilibrium is established between the pressure inside and the pressure outside of that mechanism. The initial pressure is determined in accordance with the amount of product fill in conjunction with a given container size. Whenever the pressure in the gas generating chamber 14 drops due to the expulsion of product and the concomitant expansion of the volume of the gas generating chamber, the pressure regulating mechanism expels a predetermined amount of second liquid reactant 19 which mixes with the first reactant 17 and regenerates pressure to reestablish the initially charged pressure within the gas generation chamber. The amount of citric acid or vinegar, for example, discharged is determined by the pressure differential between the container and tube head space and the volume of gas in the tube. The act of filling the product bag 12 activates the pressure regulating system, charging it to a dispensing pressure. The pressure regulating system further controls the dispensing pressure over the course of dispensing the product from the container 13.

As further shown in FIG. 1, the product bag 12 has a gusseted end 21 and is a predetermined length, dependent upon the container size. More specifically, product dispensing bag 12 is of a length such that the presence of product in the bag 12 brings a base 23b (23a is the starting position) of the gusset 21 into contact with the bottom 22 of the container 13, which may be dome shaped. The gusset 21 serves to prevent undue force on a seal between the valve 10 and the bag 12 when product 25 is in the bag. Furthermore, the gusset 21 improves bag fill capacity of the product 25 for a given can size. Preferably, the height of the gusset 21 (distance between the bottom of the bag and interior seam of the gusset) extends for approximately 80% of the radius of the container.

Figure 2:
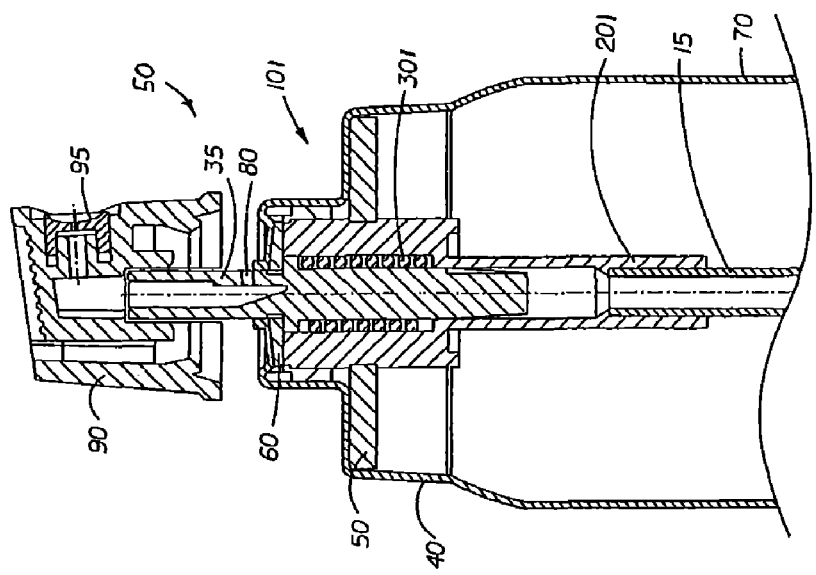
FIG. 2 is a partial cross-sectional side elevational view of a preferred metered dose valve assembly.

FIG. 2 depicts a non-limiting exemplary embodiment of a spray package 502 having a metered-dose valve assembly 101. Metered-dose valve assembly 101 has a dip tube 15 which provides a flow channel for delivery of a product (e.g., underarm product) to the valve housing 201. Valve housing 201 provides a volumetric chamber for product containment and also has a mechanical assembly area for supporting the spring 30 and stem 35. Spring 30 and stem 35 may be constructed as individual or combined parts. Spring 30 provides an energy constant to return the stem 35 to a closed/sealed position. Stem 35 provides a connection between valve housing 201 and actuator 90. In the metered valve, the stem 35 provides the function of shut off of the flow of product from the dip tube 15 and the valve housing 20. This shut off operation is achieved by designing stem 35 such that its bottom end impacts the top of dip tube 15 or bottom end of the valve housing 201 at the time of or before the stem orifice 80 opens. By designing the opening and shut off functions in this manner, only the product contained within the valve housing 201 is dispensed. Ferrule 40 mechanically fastens the metered-dose valve assembly 101 to container body 70. Valve gasket 50 provides a seal between ferrule 40 and container body 70. Stem gasket 60 provides a seal between valve housing 201 and ferrule 40, as well as a seal between stem orifice 80 and the flow of the product. Each of the gaskets in the Metered-dose valve assembly 101 may be compressed to conform between surfaces. For valve gasket 40, compression minimizes any potential leakage between ferrule 40 and container body 70. For stem gasket 60, compression minimizes any potential leakage between valve housing 201 and the environments or to stem orifice 80. Stem orifice 80 provides a flow channel from valve housing 201 to actuator 90.

Figure 3:
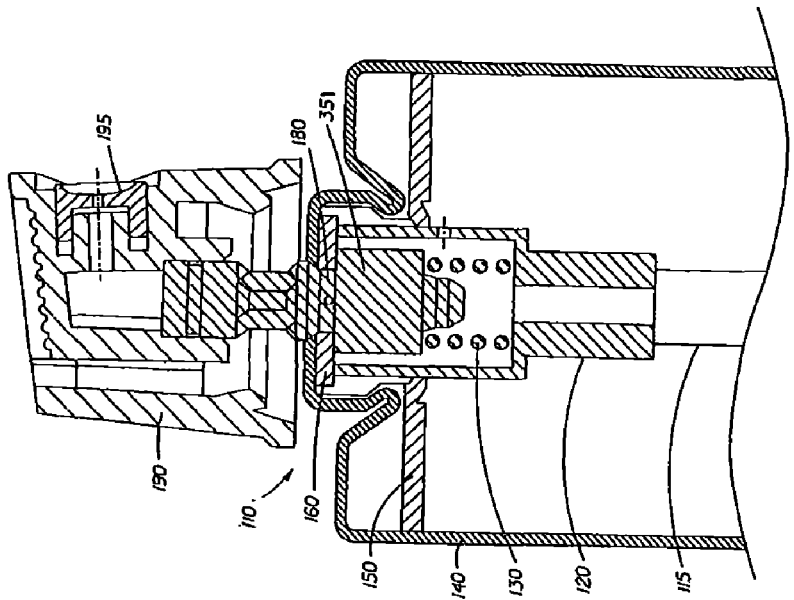
FIG. 3 is a partial cross-sectional side elevational view of a preferred continuous-flow valve assembly.

FIG. 3 depicts an example embodiment of a continuous-flow valve assembly 110. Continuous-flow valve assembly 110 has a dip tube 115 which provides a flow channel for delivery of a product (e.g., scalp medication) to the valve housing 120. Valve housing 120 has a mechanical assembly area for supporting the spring 301 and stem 351. Spring 301 and stem 351 may be constructed as individual or combined parts. Spring 301 provides an energy constant to return the stem 351 to a closed/sealed position. Stem orifice 180 provides a flow channel from valve housing 201 to actuator 190. Depressing of actuator 190 causes product to be sprayed in a continuous fashion from the package. Exit channel 195 with its valve diameter orifice provides an exit flow channel for the flow of product just before it is sprayed. It is this valve diameter orifice that is desirably about 0.001-0.10 inches, more preferably about 0.001-0.015 inches and most preferably about 0.001-0.010 inches.

To appreciate the present invention, one should recognize that the metered-dose valve assembly 101 only allows for a metered dose such that the amount of product delivered is controlled (e.g., controlled by the volume of the valve housing 201). In contrast, the continuous-flow valve assembly 100 and 110 does not control the amount dosed, rather the amount of product delivered is dependent upon the duration of time that the consumer depresses actuator 190. It should also be appreciated by one skilled in the art that the design of metered-dose valve assembly 101 may be altered in a variety of ways but that the important characteristic is that the valve assembly used must deliver controlled volumes of product (i.e., not a continuous spray).

It has also been determined that certain sizing relationships for the bag, the gusset, and the valve assembly further enhance the characteristics of the dispensing system. The bag height should be approximately equal to the difference between the inside can height (from the top rim of the container to the top surface of the bottom dome) and the valve height. Preferably, the material length is approximately equal to the sum of twice the bag height, and two times the gusset length.

Further reference is made to the following prophetic and actual examples of continuous spray medication compositions.

PROPHETIC EXAMPLE I

A 2% v/v solution of minoxidil can be prepared using the following carrier solutions:

Carrier 1:

| Ingredient | % v/v |
| --- | --- |
| SD alcohol, ethanol or isopropanol | 60.0 |
| propylene glycol, glycerin and/or dimethyl-isosorbide | 20.0 |
| purified water | 20.0 |

Carrier 2:

| Ingredient | % v/v |
| --- | --- |
| SD alcohol, ethanol or isopropanol | 16.8 |
| propylene glycol, glycerin and/or dimethyl-isosorbide | 20.0 |
| purified water | 63.2 |

Procedure

In separate mixing vessels, add the carrier solutions. Then add milled minoxidil until they are in a 2% v/v (for higher concentrations of minoxidil, proportionately higher amounts of the propylene glycol, glycerin and/or dimethyl-isosorbide would be expected to be used) solution in each mixing vessel. Continue mixing until all ingredients are added and dissolved. Add concentrate to aerosol can and charge with propellant or propellant source.

| Valving | |
| --- | --- |
| Vendor: | SeaquistPerfect |
| Type: | XT 91 |
| Stem Orifice: | 0.013" |
| Spring: | 0.025" SS |
| Body Orifice: | 0.13" XT Standard |
| Vapor Tap: | None |
| Tubing ID: | 0.122" |
| Actuator: | EUROSTAR ST VALVE 0.015" DU3832 |

PROPHETIC EXAMPLE 2

The following are two examples of metered-dose valve assemblies:
Manufactured by: Seaquist
Part #: MV20-25
25 MCL Metered Body
0.020" Stem
Buna-P Diaphragm
0.021" Spring
Buna-P Liner
Ferrule: Un-Anodized
Capillary 0.045" I.D. Dip Tube, Cut to 4" Length
Manufactured by: Seaquist
Part #: MV20-185
185 MCL Metered Body
0.020" Stem
Buna-P Diaphragm
0.021" Spring
Buna-P Liner
Ferrule: Un-Anodized
Capillary 0.045" I.D. Dip Tube, Cut to 4" Length

ACTUAL EXAMPLE 3

A bag-in-can package supplied by CCL Container, Canada (now Seaquist) was prepared with #10 cans and 30 psi pressure (compressed air) prior to filling the bag with 1 oz. 5% minoxidil (OTC). The pressure rose to 100 psi when the bag was full. Two actuator valve sizes of 0.009 inches and 0.013 inches were interchangeably used on the same can to produce the following data (gassing was observed visually).

| ACTUAL VALVE SIZE (INCHES) | TIME TO DISPENSE | DISPENSE VOLUME (ML) | RATE (ML/SEC) | GASSING |
|---|---|---|---|---|
| .009 | 1.97 | 1.0 | .5 | LOW |
|  | 2.41 | 1.2 | .49 | LOW |
|  | 1.97 | 1.0 | .5 | LOW |
| .013 | 2.28 | 2.4 | 1.05 | LOW |
|  | 2.1 | 2.0 | .95 | LOW |

Because of the goal of dispensing about 1 mL of product within about 1-5 seconds, preferably about 1-3 seconds, and more preferably, about 2 seconds, the 0.009 inch valve appears to provide the closest match for optimal performance, low gassiness (preferably less than 5% respirable drops per mL of dispensing) and ideal dosage within typical consumer actuation time limits. Ideally, the actuator valve should be less than 0.015 inches in diameter, and more preferably less than 0.010 inches in diameter, with flow rates of about 0.2-1 mL/sec or less, and preferably about 0.5 mL/sec or less. The actuator valve diameter is generally less than 0.10 inches to prevent accidental overdosing, but greater than 0.001 inches to minimize gassing. More preferably, the valve actuator diameter can be less than 0.015 inches and greater than 0.001 inches, and especially about 0.006, 0.007, 0.008 and 0.009 inches in diameter.

Although the invention has been described in terms of exemplary embodiments, it is not limited thereto. Rather, the appended claims should be construed broadly to include other variants and embodiments of the invention that may be made by those skilled in the art without departing from the scope and range of equivalents of the invention.

What is claimed is:

1. A method of treating alopecia, comprising:
providing a delivery system comprising a valve assembly affixed to a portable container containing a pressure source surrounding a product bag containing minoxidil in an amount sufficient to stimulate or maintain hair growth, said minoxidil disposed within a pharmacologically acceptable carrier solution;
rotating said container and said valve assembly such that said valve assembly is at least partially below a portion of said container;
actuating said valve assembly whereby said pressure source surrounding said product bag is used to force said minoxidil and said carrier solution out of the bag; and
continuously spraying a fine mist of said minoxidil and said carrier solution onto an alopecia affected area of a scalp, whereby said fine mist contains about 1 mL of said minoxidil and said carrier solution, and said continuous spraying step is less than 5 seconds in duration.

2. The method of claim 1 wherein said method does not require contact between the scalp owner's hand and said minoxidil.

3. The method of claim 2 wherein said fine mist comprises liquid droplets having an average diameter of about 1 nanometer to about 200 micrometers.

4. The method of claim 1 wherein said fine mist comprises about 20 mg to 150 mg minoxidil per mL.

* * * * *